United States Patent [19]

Kapp

[11] 4,325,938

[45] Apr. 20, 1982

[54] PESTICIDE AND PROCESS FOR ITS PRODUCTION

[75] Inventor: Wolfgang Kapp, Offenbach am Main, Fed. Rep. of Germany

[73] Assignee: Deutsche Gesellschaft für Schädlingsbekämpfung mbH, Frankfurt am Main, Fed. Rep. of Germany

[21] Appl. No.: 136,363

[22] Filed: Apr. 1, 1980

Related U.S. Application Data

[63] Continuation of Ser. No. 968,089, Dec. 11, 1978, abandoned, which is a continuation of Ser. No. 627,023, Oct. 30, 1975, abandoned.

[30] Foreign Application Priority Data

Nov. 15, 1974 [DE] Fed. Rep. of Germany ....... 2454172

[51] Int. Cl.$^3$ ..................... A01N 25/00; A01N 25/26; A01N 25/10
[52] U.S. Cl. ........................................ 424/18; 424/27; 424/32
[58] Field of Search .............................. 424/32, 27, 18

[56] References Cited

U.S. PATENT DOCUMENTS

3,719,751 3/1973 Rauscher et al. ..................... 424/27
3,866,347 2/1975 Schoom ................................ 424/27

FOREIGN PATENT DOCUMENTS

1531677 3/1968 France ................................. 424/27

*Primary Examiner*—Frederick E. Waddell
*Attorney, Agent, or Firm*—Gordon W. Hueschen

[57] ABSTRACT

The present invention relates to a pesticide comprising a molded body made of a water-insoluble organic solid substance in which at least one finely divided metal phosphide is embedded, the molded body being coated on at least one side with a fibrous substance which is permeable to water vapor and the fibers of which at least partially extend as far as the embedded phosphide particles, and to a process for producing such a pesticide.

18 Claims, 1 Drawing Figure

PESTICIDE AND PROCESS FOR ITS PRODUCTION

This application is a continuation of my prior-filed co-pending application Ser. No. 968,089, filed Dec. 11, 1978, which in turn is a continuation of Ser. No. 627,023, filed Oct. 30, 1975, both now abandoned.

BACKGROUND OF THE INVENTION

The present invention relates to pesticides.

More particularly, the present invention relates to a pesticide comprising a molded body made of a water-insoluble organic solid substance in which one or more finely divided metal phosphides, preferably aluminum phosphide and/or magnesium phosphide, are embedded, and to a process for producing such a pesticide.

PRIOR ART

French Patent Specification No. 1,531,677 describes molded bodies, e.g. tablets or pellets, which are used as insecticides. These comprise finely divided metal phosphides, preferably the phosphides of aluminum and magnesium, especially with particle diameters of 10 1,000 microns, which are embedded in a polyester resin, polyurethane resin, polyvinyl resin or polystyrene resin. These molded bodies may contain 30 to 60 percent by weight of the mtal phosphide/phosphides.

The disadvantage of these insecticides is that they give off gas slowly. When brought into an atmosphere having 60 percent relative humidity at room temperature, compositions having 60 or 50 percent by weight of aluminum phosphide and magnesium phosphide and having 40 or 50 percent by weight of polyester resin, frequently release the full amount of gas only after approximately twenty days. It is obvious, therefore, that a long time is needed before the residues do not contain any considerable quantities of phosphides and can therefore be removed and eliminated safely, and that the concentration of hydrogen phosphide in the gas-filled room is only very low because of the slow release of gas with a given quantity of the composition.

The present invention seeks to provide pesticides of the type mentioned such that they release gas more quickly and can be removed easily and completely from the gas-filled room after the release of gas.

DETAILED DESCRIPTION OF THE INVENTION

Figure 1:
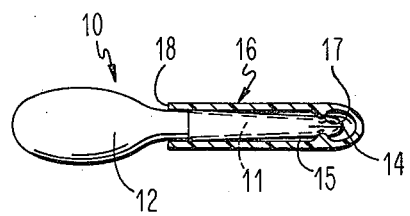
Figure 2:
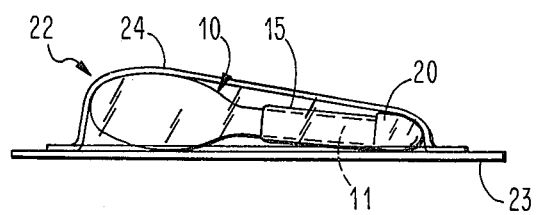
Figure 3:
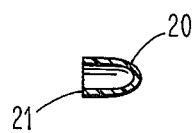

According to the present invention, this aim may be achieved in that the molded body is coated on one or more sides with a fibrous substance which is permeable to water vapor and the fibers of which at least partially extend as far as the embedded phosphide particles.

These fibers which extend to the inside of the molded bodies act as "wicks", by means of which the atmospheric moisture reaches at least some of the phosphide particles. The particles of the metal phosphides thus decompose with the development of gaseous hydrogen phosphide and with an increase in volume. Consequently, the water-insoluble organic solid substance around the remaining phosphide particles is shattered and a regulated and quick release of gas takes place.

The pesticides of the present invention preferably contain as the water-insoluble organic solid substance a thermoplastic substance, such as polyethylene, polypropylene, hard paraffin, polyvinyl chloride, polyvinyl acetate, polystyrene, copolymerisates of vinyl acetate and vinyl chloride, copolymerisates of polyethylene, polystyrene, polypropylene, polyvinyl chloride and other polyvinyl compounds, or similar compounds with other copolymerizable material. Any other thermoplastic substance is suitable. The substance must be thermoplastic, since otherwise it is not possible to achieve a penetration of the fibrous substance employed.

Finely divided aluminum phosphide and/or magnesium phosphide having particle diameters up to $300\mu$ have proved to be particularly suitable.

Good results are obtained with pesticides which contain 60 to 120 parts by weight of the water-insoluble organic solid substance per 100 parts by weight of the metal phosphide. The release of gas is usually slower than desirable when the content of water-insoluble organic solid substance is increased, and it frequently occurs too quickly and even during the time needed for positioning, placing, or exposing the pesticide for application when a smaller content is present.

The fibrous substance which coats the molded body on one or more sides may, for example, be a fabric, a felt, or a non-woven fabric. Fibrous substances made of cellulose, such as cotton fibers, wood pulp, regenerated cellulose, or the like, are particularly suitable. These substances conduct the atmospheric moisture into the interior of the molded bodies particularly well.

The pesticide according to the present invention is preferably in the shape of a plate, a band, or a strip. It is therefore easily possible to bring the respective desirable quantities of the composition into the room which is to be filled with gas, e.g., by cutting off the desired lengths from a band.

The plate, the band, or the strip is preferably 3 to 9 mm. thick.

A particular embodiment of the present invention relates to a process for the production of such a pesticide. The process is characterized in that a layer comprising a mixture of the at least one finely divided metal phosphide and the water-insoluble organic solid substance is applied to a layer of the fibrous substance, the composite then being heated to such a high temperature and for so long that a molded body is produced from the thermoplastic water-insoluble organic substance and the at least one phosphide and this molded body becomes joined to the layer of the fibrous substance, the thermoplastic organic substance hardening upon being allowed to cool to room temperature.

Thus, the whole may, for example, be heated at a temperature of from approximately 140° to 160° C. and for a time of from approximately 3 to 8 minutes, and then allowed to cool.

If it is desirable to produce a layered body which is coated with a fibrous substance on two sides, then a second layer of a fibrous substance is rolled onto the molded body while it is warm and plastic.

The process may be carried out continuously or discontinuously.

The pesticides of the present invention may be used to fill, with gas, rooms where there may even be, for example, cereals, tobacco, foodstuffs, or luxury foodstuffs. The hydrogen phosphide which is thus developed destroys all pests such as insects or rodents.

The present invention will now be further described with reference to the following Example.

EXAMPLE

A layer, approximately 7 mm. thick, of aluminum phosphide having particle diameters of 10 to $300\mu$ and granulated polyvinyl acetate in the weight ratio of 80 parts of polyvinyl acetate, containing plasticizers, to 100 parts of aluminum phosphide is applied to a layer, 0.2 mm. thick, of non-woven fabric comprising cellulose fibers. The composite is heated to 160° C. for approximately 5 minutes by means of an infra-red radiator.

A second layer of the non-woven fabric, which serves as the under layer, is rolled onto the surface of the molded body thus produced while it is still hot, by means of a roller heated to approximately 150° C. and for a period of approximately 1 minute. Upon cooling to room temperature, a plate which is 4 mm. thick is produced.

When this molded body is brought into an atmosphere of 65 percent relative humidity at a room temperature of 20° C., gas is released from the phosphide contained in the composition at the rate of 1.2 percent of the total amount of phosphide after two hours, 9.5 percent after five hours and 21 percent after ten hours, the greatest possible release of gas being achieved after seventy-two hours. At the end of this time, the aluminum phosphide contained in the pesticide has been decomposed to the extent of approximately 96 percent with consequent evolution of phosphide to the same extent.

In the same manner, similar advantageous products and results are obtained when: the phosphide is magnesium phosphide or a mixture of aluminum phosphide and magnesium phosphide; the organic solid substance is polyethylene, polypropylene, polyvinyl chloride, hard paraffin, polyvinyl acetate, polystyrene, copolymerisates of vinyl acetate and vinyl chloride, copolymerisates of polyethylene, polystyrene, polypropylene, polyvinyl chloride and other polyvinyl compounds, or similar compounds with other copolymerizable material; the fibrous substance comprises, partly or completely, cellulose fibers such as cotton fibers, wood pulp, or regenerated cellulose, a fabric or a felt; the material is in the form of a strip or band instead of a plate; the strip, band, or plate varies from 3 to 9 mm. in thickness; the phosphide particles are up to 300μ particle diameter; and especially when the water-insoluble organic solid substance is present in an amount of 60 to 120 parts per about 100 parts by weight of the metal phosphide.

The present invention will now be further illustrated by way of the accompanying drawing which shows, on an enlarged scale, a section through a pesticide according to the present invention.

In the FIGURE, particles 2 of aluminum phosphide are embedded in a plate 1 comprising polyvinyl acetate. On the surface there is a non-woven fabric 3 comprising cellulose fibers, the fibers of which extend to a portion of the embedded phosphide particles.

It is to be understood that the invention is not to be limited to the exact details of operation or exact compounds, compositions, methods, or procedures shown and described, as obvious modifications and equivalents will be apparent to one skilled in the art.

I claim:

1. A pesticide comprising molded body made of a water-insoluble thermoplastic polyvinylacetate in which finely divided magnesium phosphide is embedded with the particles of said metal phosphide being dispersed in said molded body, the molded body being coated on both sides with a nonwoven fabric comprising cellulose fibers which is permeable to water vapor and fibers of which substance extend into said body into contact with metal phosphide particles contained therein.

2. A pesticide as claimed in claim 1, in which the magnesium phosphide have a particle diameter up to 300μ.

3. A pesticide as claimed in claim 1, in which the polyvinylacetate is present in an amount of 60 to 120 parts by weight per 100 parts by weight of the metal phosphide.

4. A pesticide as claimed in claim 1, in which the fibrous substance comprises wholly cellulose fibers.

5. A pesticide as claimed in claim 1, which is in a form selected from a plate, a band, and a strip.

6. A pesticide as claimed in claim 5, in which the form is 3 to 9 mm. thick.

7. A process for producing a pesticide in which process a layer comprising a solid particulate mixture of finely divided magnesium phosphide and a water-insoluble thermoplastic polyvinylacetate is applied to a layer of a nonwoven fabric comprising cellulose fibers which is permeable to water vapor, and the composite is then heated to a sufficiently high temperature for a sufficient length of time so that a molded body is produced from said mixture of water-insoluble thermoplastic polyvinylacetate and the phosphide and this molded body becomes joined to the layer of the fibrous substance, so that fibers of said fibrous substance extend into said body into contact with phosphide particles contained therein, and then providing a second layer of said fibrous substance and adhering the same to said layer comprising said thermoplastic polyvinylacetate while said thermoplastic-comprising layer is still adhesive, so as to provide said molded body with a layer of said fibrous substance on both sides thereof.

8. A process as claimed in claim 7, in which the said composite is heated to a temperature of approximately 140° to 160° C.

9. A process as claimed in claim 7, in which the said composite is heated for a period of from approximately 3 to 8 minutes.

10. A process as claimed in claim 7, in which the second layer of a fibrous substance is rolled onto the molded body while it is warm and plastic.

11. A process as claimed in claim 7, in which the magnesium phosphide has a particle diameter from about 10 to 300μ.

12. A process as claimed in claim 7, in which the water-insoluble thermoplastic organic solid substance is present in an amount of 60 to 120 parts by weight per 100 parts by weight of the metal phosphide.

13. A process as claimed in claim 7, in which the fibrous substance comprises wholly cellulose fibers.

14. A process as claimed in claim 7, in which the pesticide is in a form selected from a plate, a band, and a strip.

15. A process as claimed in claim 14, in which the form is 3 to 9 mm. thick.

16. A process as claimed in claim 7, in which the said composite is heated to a temperature sufficient to melt the water-insoluble thermoplastic substance to a point where it penetrates fibers of the fibrous substance employed.

17. A pesticide comprising a molded body made of a water-insoluble, essentially solvent-free thermoplastic polyvinylacetate in which finely-divided magnesium phosphide is embedded, with the particles of phosphide being dispersed in said molded body, the molded body being adhered on both sides to a nonwoven fabric comprising cellulose fibers substance which is permeable to water vapor and which functions as a wick therefor, fibers of the fibrous substance extending into said body into contact with metal phosphide particles contained therein.

18. A process for producing a pesticide, in which process a layer, comprising a solid particulate mixture of finely-divided magnesium phosphide and a water-insoluble essentially solvent-free thermoplastic polyvinylacetate, is applied to a layer of a fibrous substance which is permeable to water vapor and which functions as a wick therefor, the composite is then heated to a sufficiently high temperature for a sufficient length of time so that a molded body is produced from said mixture of polyvinylacetate and phosphide and becomes adhered to the layer of the fibrous substance, so that fibers of said fibrous substance extend into said body into contact with phosphide particles contained therein, and then providing a second layer of said fibrous substance and adhering the same to said layer comprising said thermoplastic polyvinylacetate while said thermoplastic comprising layer is still adhesive, so as to provide said molded body with a layer of fibrous substance on both sides thereof.

* * * * *

UNITED STATES PATENT AND TRADEMARK OFFICE
CERTIFICATE OF CORRECTION

PATENT NO. : 4,325,938
DATED : April 20, 1982
INVENTOR(S) : Wolfgang Kapp

It is certified that error appears in the above—identified patent and that said Letters Patent is hereby corrected as shown below:

Delete the sheet of drawing and substitute the attached sheet therefor.

Signed and Sealed this

Fifth Day of April 1983

[SEAL]

Attest:

Attesting Officer

GERALD J. MOSSINGHOFF

Commissioner of Patents and Trademarks

Patent No. 4,325,938
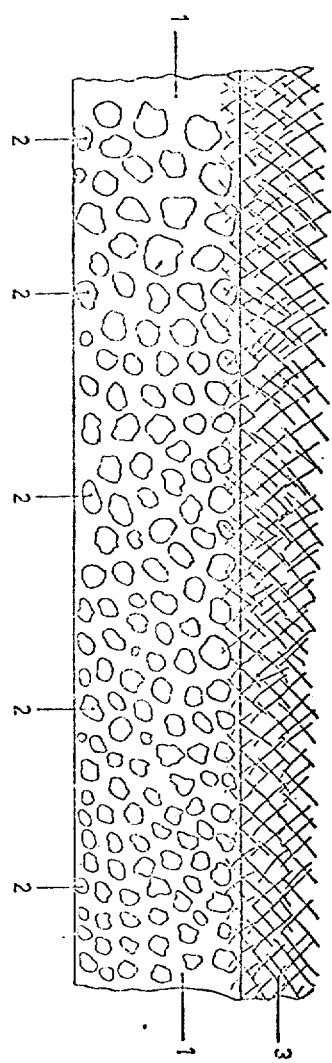

UNITED STATES PATENT AND TRADEMARK OFFICE
CERTIFICATE OF CORRECTION

PATENT NO.  : 4,325,938
DATED       : April 20, 1982
INVENTOR(S) : Wolfgang Kapp It is certified that error appears in the above-identified patent and that said Letters Patent is hereby corrected as shown below:

Col. 1, line 24; insert -- to --after "10".

Col. 1, line 28; "mtal" should read -- metal --.

Col. 4, line 42; "change "fibrous substance" to read -- nonwoven fabric comprising cellulose fibers --.

Col. 5, line 1; delete "substance".

Signed and Sealed this

Fourteenth Day of June 1983

[SEAL]

Attest:

DONALD J. QUIGG

Attesting Officer    Acting Commissioner of Patents and Trademarks